United States Patent [19]
Cocozza

[11] 3,991,761
[45] Nov. 16, 1976

[54] INHALER FOR POWDERED MEDICAMENTS

[76] Inventor: Salvatore Cocozza, via San Gimigano 4/A, Milan, Italy

[22] Filed: Oct. 21, 1974

[21] Appl. No.: 516,829

[30] Foreign Application Priority Data
Mar. 18, 1974   Italy .................................. 86249/74

[52] U.S. Cl. ............................... 128/266; 128/208
[51] Int. Cl.² ................. A61M 13/00; A61M 15/06
[58] Field of Search .................... 128/266, 208, 206

[56] References Cited
UNITED STATES PATENTS

| | | |
|---|---|---|
| 3,635,219 | 1/1972 | Altounyan ......................... 128/266 |
| 3,669,113 | 6/1972 | Altounyan ......................... 128/266 |
| 3,807,400 | 4/1974 | Cocozza ............................. 128/266 |

FOREIGN PATENTS OR APPLICATIONS 1,331,216   9/1973   United Kingdom ................. 128/266

*Primary Examiner*—Aldrich F. Medbery

[57] ABSTRACT

An inhaler for powdered medicaments contained in a capsule which is inserted when needed into an elongated recess by rotatably moving two component portions out of register, perforated by means of biasedly attached piercing devices, and emptied by spinning within a cylindrical spinning chamber when air is drawn through tangentially disposed intake passages, the component portions being held in register by a latching device.

18 Claims, 13 Drawing Figures

INHALER FOR POWDERED MEDICAMENTS

FIELD OF THE INVENTION

The present invention relates to inhalers, and particularly relates to an inhaler for the administration of powdered medicaments.

SUMMARY OF THE INVENTION

According to the present invention, there is provided an inhaler for the adminstration of powdered substances comprising a body portion having a chamber for receiving a capsule containing powdered substances, piercing devices on the body portion operable to perforate a capsule in the capsule chamber, and air intake passages communicating with the capsule chamber and positioned in such a manner that air drawn therethrough when inhaling air through an inhaler passage leading from the chamber imparts a rotary and shaking motion to a capsule in the capsule chamber.

Embodiments of the present invention can be constructed in two main parts, a body portion of the inhaler and a tubular portion or mouth-piece: these two portions are rotatably connected and releasably latched to each other to allow access to the interior of the body portion so as to place a capsule containing the substance for inhalation in position in the capsule chamber. Following perforation of the capsule by the piercing devices, inhalation by the patient through the tubular portion or mouth-piece causes the powder to be drawn out of the capsule and entrained in the inhaled air.

Preferably, the air intakes are positioned so that intake air passes tangentially into the capsule chamber. In the preferred embodiment of the invention, the capsule chamber has an elongated recess in the bottom wall thereof, in which recess the capsule in the chamber rests when the inhaler is not in use, and the air intake is drawn from the recess into the capsule chamber by the air passing through the capsule chamber from the intake passages to the inhalation passage upon inhalation. The inhaler of the present invention is convenient and simple to use, of constant efficiency thereby ensuring a consistent dosage, and of small size.

The body portion and tubular portion are preferably pivotally attached together, and in the preferred embodiment this is effected by means of a pivot pin, the axis of which is parallel to the axis of the tubular portion by which is eccentrically placed on one side thereof to allow disengagement or locking by a simple revoloution of one portion with respect to the other about an axis parallel to the axis of the tubular portion of the inhaler.

Preferably, the piercing devices comprise movable pushbuttons, each carrying a set of elongated spikes positioned to enter a capsule in the recess within the capsule chamber and to effect perforation thereof upon depression of a push button. In the preferred embodiment, there are two such push buttons, each being maintained in a normal position by four independent springs, and each being held in place by rims on the body portion which engage cooperating shoulders on each push button. Each of the push buttons supports four elongated metal spikes. Perforation of a capsule in the elongated recess at the bottom of the capsule spinning chamber is thus simply effected by a simple pressure on one or both of the push buttons.

The shape of the elongated recess in the bottom wall of the capsule is preferably substantially the same as that of a conventional medicament capsule, the recess being generally rectangular with rounded ends. Preferably the spikes or pins of the piercing devices are coaxial with the recess so that a capsule is perforated at its ends. The capsule chamber is preferably circular so that a pierced capsule is caused to rotate solely by the tangential intake air upon inhalation. The intake air also acts to draw the capsule out of the recess upon inhalation so that operation is effectively automatic. The diameter of the capsule chamber is slightly larger than the length of a conventional medicament capsule so that there is a small clearance between the chamber and the ends of the capsule as it rotates; this causes a shaking of the capsule as it strikes against the cylindrical wall of the capsule chamber, thereby urging the powder out from the capsule and causing it to be mixed with the intake air upon inhalation.

The tubular portion of the inhaler consists essentially of a circular pipe having at one end a base supporting an abutment stop for locating the inhaler body. The base of the tubular portion forms, when the parts of the inhaler are assembled together, the upper part of the capsule chamber and has a slightly concave surface for facilitating the rotation of a capsule. At the opening of the inhalation passage of the tubular portion there is a grating, suitably dimensioned to optimize the air/powdered substance ratio.

BRIEF DESCRIPTION OF THE DRAWINGS

One embodiment of the invention will now be more particularly described, by way of example, with reference to the accompanying drawings, in which.

DESCRIPTION OF THE PREFERRED EMBODIMENT

Figure 1:
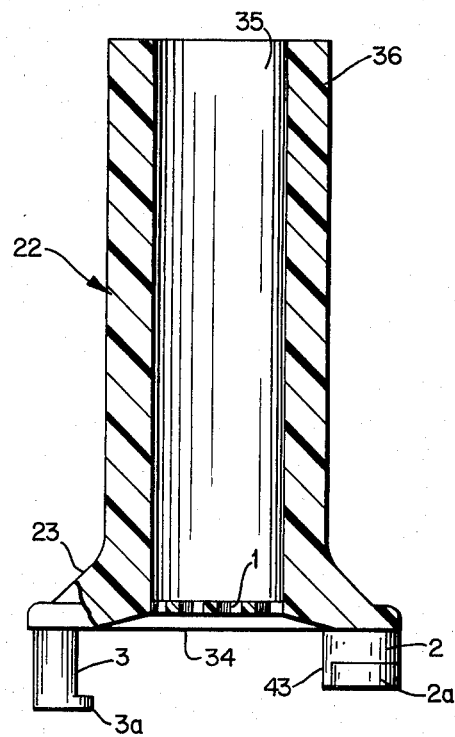
FIG. 1 is an axial section of the mouth-piece of an inhaler formed as an embodiment of the invention.

Referring now to the drawings, the inhaler shown comprises a body portion 21 and a mouth-piece 22.

The mouth-piece 22 has an ellipsoidal tubular portion, with walls 36 and inhalation passage 35, and an enlarged basal end 23 which engages the upper face 33 of the body portion 21. The mouth-piece 22 is connected to the body portion 21 by means of a pivot pin 3, projecting from the basal end 23 of the mouth-piece 22, which fits into a hole 13 in the body portion 21. The pivot pin 3 and hole 13 are aligned with one another when the mouth-piece 22 and body portion 21 are assembled and have a common pivotpin axis. The pivot pin 3 and hole 13 are each respectively disposed eccentrically to the longitudinal axis of the mouth-piece 22 and body portion 21.

At the end of the pivot pin 3 is a lateral projection 3a1 The hole 13 has a lateral enlargement 13a and at the lower end thereof has an enlarged annular section 13b. The lateral projection 3a of the pivot pin 3 passes down the lateral part 13a of the hole 13 upon insertion of the pin 3 into the hole 13 when the pivot pin 3 and hole 13 are in register. Upon relative rotation of the body portion 21 and the mouth-piece 22, this lateral projection 3a is moved out of register with the lateral part 13a of the hole 13 and into engagement with the shoulders at the end thereof formed by the enlargement 13b.

The position of the lateral projection 3a and the lateral part 13a is, in each case, such that the mouth-piece 22 and body portion 21 can be relatively revolved about the pivot-pin axis of the pivot pin 3 and hole 13 between an operating position in which the basal end 23 of the mouth-piece 22 is in register with the upper face 33 of the body portion 21, and a loading position where a chamber 10 in the body portion 21 is exposed without bringing the lateral portion 3a of the pivot pin 3 into register with the lateral part 13a of the hole 13 so that, in use of the inhaler, the two portions 21 and 22 can remain fixed to one another, but the two portions 21,22 may be separated from one another entirely if desired by relative revolution of the two portions to bring the cooperating projections 3a and part 13a into register.

Figure 6:
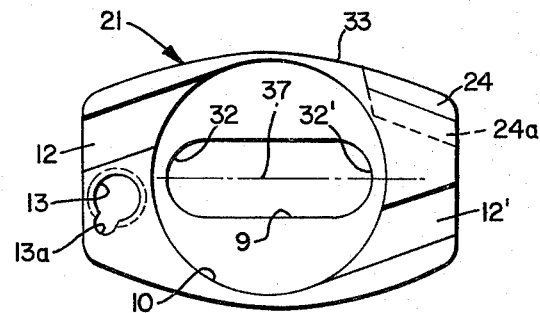
FIG. 6 is a plan view of the body portion of the inhaler.

The body portion 21 of the inhaler is formed, as mentioned above, with a recess 10 having a circular cross section, in the lower wall of which there is an elongated recess 9 which has substantially the same shape as a conventional medicament capsule, as can be seen clearly in FIG. 6. There are two narrow recesses 12, 12' in the upper face 33 of the body portion 21. These recesses 12, 12' communicate tangentially with the recess 10, as can be clearly seen in FIG. 6. When the mouth-piece 22 and the body portion 21 of the inhaler are assembled in operating position, the lower face 34 of the basal portion 23 of the mouth-piece 22 closes the recess 10 to define a capsule spinning chamber 10. Similarly, the recesses 12, 12' are closed by the lower face 34 of the basal portion 23 to form air inlets or passages 12, 12' to the capsule spinning chamber 10. In other words, combining the mouth-piece 22 and the body portion 21 to form the inhaler of this invention covers the recesses 10, 12 and 12' to form the chamber 10 and the air inlets 12, 12'.

At the lower end of the inhalation passage defined by the mouth-piece 22, there is secured a grating 1 which prevents a capsule in the capsule chamber 10 from being drawn up the mouth-piece 22 upon inhalation. There is thus open communication between the inhalation passage 35 of the mouth-piece 22, the capsule chamber 10, and the air inlets 12 and 12'.

Figure 2:
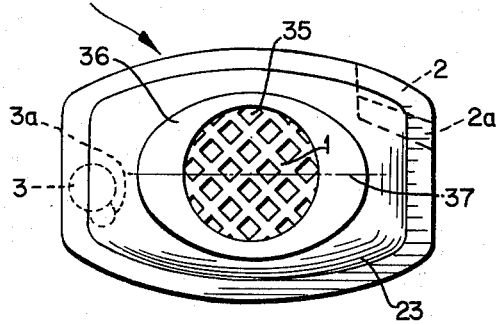
FIG. 2 is a plan view of the mouth-piece shown in FIG. 1.
Figure 3:
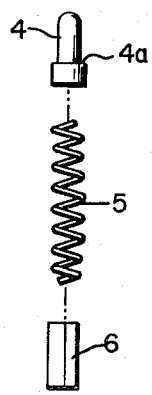
FIG. 3 is a side view of three elements forming a spring-lock device for holding the mouth-piece and a body portion of the inhaler in operating relationship.

FIG. 3 illustrates a suitable form of latching device for holding the mouth-piece 22 and body portion 21 in operating relationship. As will be seen from FIG. 1, the basal portion 23 of the mouth-piece 22 has a projection 2 on the side thereof opposite the pivot pin 3; this projection 2 is L-shaped when viewed from the right side of FIG. 1 and is obliquely disposed to the major axis 37 of the ellipsoid formed by the walls 36, as seen in phantom in FIG. 2. The projection 2 has a latching lug 2a which projects laterally. The body portion 21 has an L-shaped recess 24 which is obliquely disposed to the major axis 37 of the ellipsoidal recess 9 and has a latching slot 24a which projects laterally. The L-shaped projection 2 of the basal portion 23 of the mouth-piece 22 slides into L-shaped recess 24 in the upper part of the body portion 21 when the mouth-piece 22, viewed as in FIG. 2, is revolved clockwise around the body portion 21, viewed as in FIG. 6, and is held in position by the latching device illustrated in FIG. 3.

Figure 7:
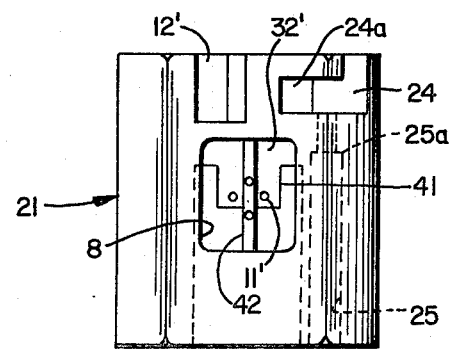
FIG. 7 is a side view of the body portion of the inhaler taken on the line 9—9 of FIG. 5.
Figure 8:
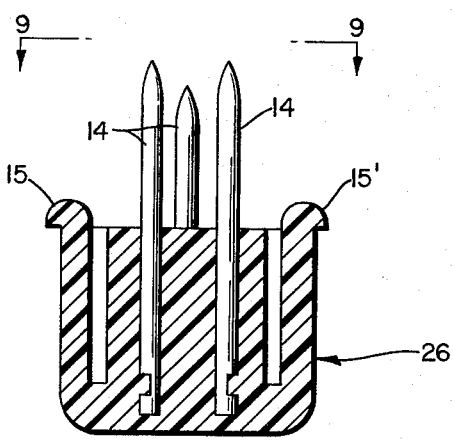
FIG. 8 is a sectional view of a push button which is attached to the body portion of the FIGS. 4 through 7.
Figure 9:
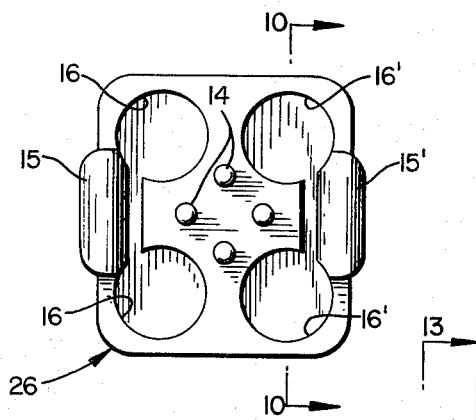
FIG. 9 is an end view taken on the line 9—9 of the push button of FIG. 8.
Figure 10:
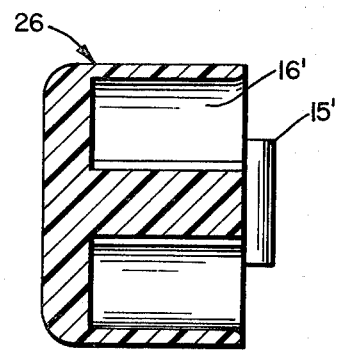
FIG. 10 is a sectional view taken on the line 10—10 of FIG. 9.

The latching device comprises a plunger 4 having a convexly curved end, a compression spring 5, and a plug 6. These elements are housed in a bore 25 in the body portion 21 which is visible in FIGS. 4 and 7. This bore 25 opens into the lower face of the L-shaped recess 24. The plunger 4 has a shoulder 4a which engages a corresponding shoulder 25a near the upper end of the bore 25 to determine the maximum amount by which the convexly curved end of the plunger 4 can project from the opening formed by the bore 25 into the L-shaped recess 24. When the mouth-piece 22 is revolved to the locked position, the lateral projection 2a extends into the latching slot 24a and displaces the plunger 4 downwardly against the action of the compression spring 5 which thus acts to lightly latch the projection 2 in place in the recess 24, thereby holding the mouth-piece 22 and body portion 21 together in the closed or operating position.

Figure 4:
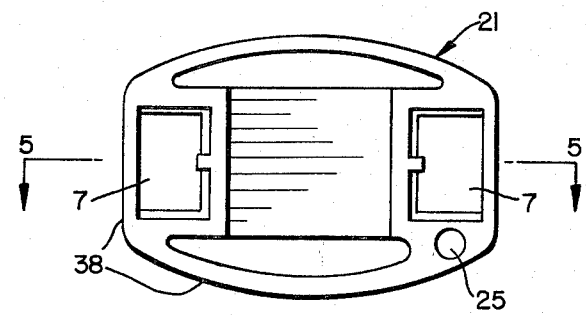
FIG. 4 is a bottom view of the body portion of the inhaler.
Figure 5:
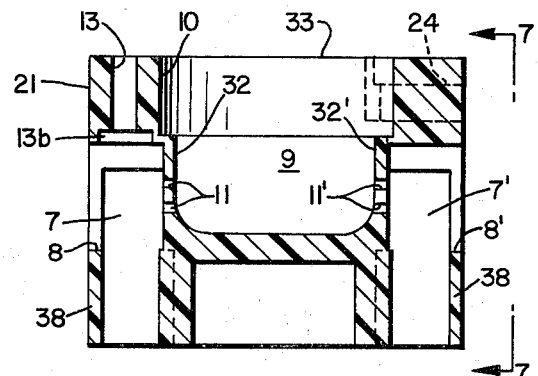
FIG. 5 is an axial section of the body portion of the inhaler taken on the line 5—5 of FIG. 4.
Figure 11:
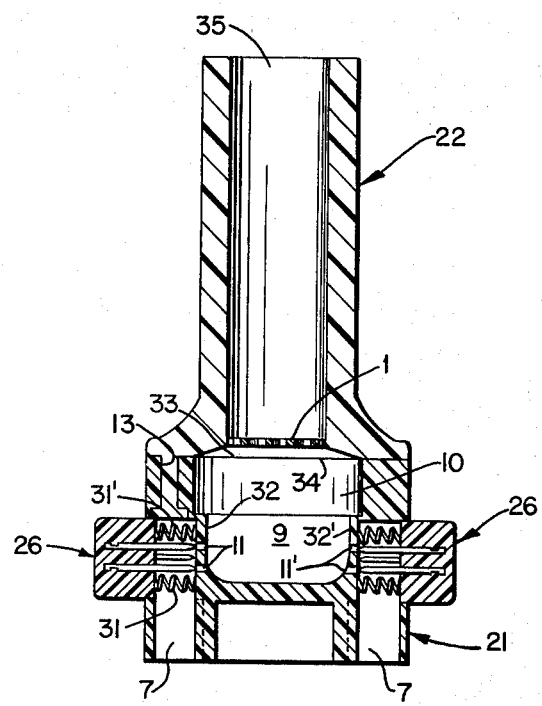
FIG. 11 is an axial sectional view of an assembled inhaler.
Figures 12, 13:
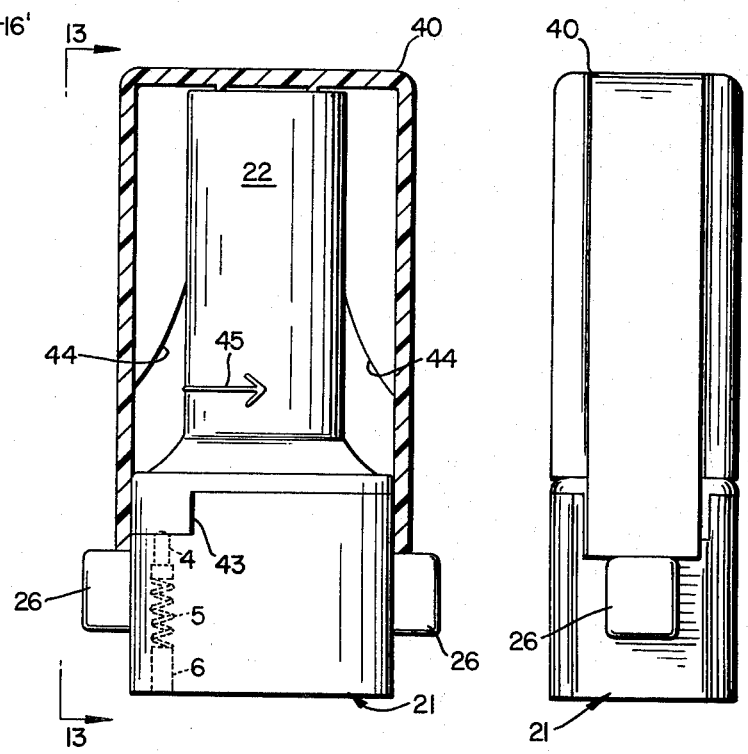
FIG. 12 is an axial partially sectioned view similar to that of FIG. 11, showing the inhaler with a cap in position.
FIG. 13 is a side view, taken on the line 13—13 of FIG. 12 of the inhaler with the cap in position of FIG. 12.

In line with the ends of the capsule recess 9, in the bottom of the recess 10, are located two push buttons 26 which each carry four sharpened metal pins 14 which project inwardly towards the capsule recess 9, as shown in FIG. 11–13. The body portion 21 is formed with two rectangular section galleries 7, 7', as shown in FIGS. 4 and 5, which have openings 8, 8' aligned with the end of the capsule recess 9. Each push botton 26 has a pair of shoulders 15, 15' which are located against the rims of an opening 8 or 8' in the outer wall 38 of the body portion 21 and held in position by four biasing springs 31, 31' which are mounted in respective recesses 16, 16' in the push buttons 26. The inner walls 32, 32' of the galleries 7, 7', between the galleries 7, 7' and the capsule recess 9, are provided with four openings 11, 11' aligned with the sharpened metal pins 14.

Pressure applied to the push buttons 26, to compress the biasing springs 31, 31' which locate them in position, urges the sharpened metal pins 14 through openings 11, 11' and into the capsule recess 9. When a capsule is positioned in the recess 9, it is held against movement because the recess 9 is only slightly larger than the capsule itself, and thus the sharpened metal pins 14 penetrate and perforate the two ends of the capsule, permitting the powdered medicament to pass out through these perforations after the push butttons 26 have been released.

As shown in FIGS. 12 and 13, the inhaler is fitted with a conventional cap 40 which covers the mouth-piece 22 and rests against the open end of the mouth-piece 22 and against the two pushbuttons 26. It is centered with respect to the 44, as is known in the art.

In operation of the inhaler, the mouth-piece 22 is opend in a counter-clockwise direction 45. As seen in FIGS. 2 and 6, the moth piece 22 is revolved about the hole 13 to expose the recess 10 and the capsule recess 9. A capsule is dropped into the capsule recess 9. The mouth-piece 22 and body portion 21 are then closed by clockwise revolution of the mouth-piece 22, as seen in FIG. 2, about the hole 13 in the body portion 21 until the projection 2 engages the recess 24 and the lug 2a fits into the latching slot 24a so that the projection 2 is latched in position by the plunger 4. The push bottons 26 are then depressed, either individually or together, to perforate the ends of the capsule in the capsule recess 9.

Administration of the powdered medicament can then take place simply by inhaling through the mouth-piece 22 which can be applied either to the mouth or to a nostril. The rush of air through the inlets 12, 12' upon inhalation causes a vortex in the capsule chamber 10 due to the fact that the inlets 12 and 12' are positioned substantially tangentially with respect to the circular section capsule chamber 10. The vortex in the capsule chamber 10 lifts the perforated capsule out from the capsule recess 9 and causes the capsule to spin rapidly about the longitudinal axis of the inhaler. Because the length of the capsule is slightly less than the diameter of the capsule chamber 10, there are repeated impacts between the ends of the capsule and the side wall of the chamber 10 which causes powdered medicaments from within the capsule to be drawn out through the perforations in the ends of the capsule, this being assisted by the spinning motion of the capsule itself, and the powder is entrained with the air passing through the grating 1 and along the inhalation passage 35 of mouth-piece 22.

Because it will be readily apparent to those skilled in the art that innumerable variations, modifications, applications, and extensions of these embodiments and principles can be made without departing from the spirit and scope of the invention, what is herein defined as such scope and is desired to be protected should be measured, and the invention should be limited, only by the following claims.

What is claimed is:

1. An inhaler for powdered medicaments comprising:
    A. an elongated mouth-piece comprising a coaxially disposed inhalation passage;
    B. a body portion comprising:
        1. a chamber which is adapted to receive a capsule containing said medicaments and which is open communication with said inhalation passage, and
        2. an air intake passage which is tangentially disposed to said chamber;
    C. a pivot means, for pivotably connecting said mouth-piece and said body portion, comprising:
        1. a hole within said body portion which is eccentrically disposed with respect to said chamber, and
        2. a pivot pin which:
            a. fits rotatably within said hole so that said pin and said hole are aligned when said pin and said hole are in register,
            b. has a pivot-pin axis which is parallel to the axis of said mouth-piece, and
            c. is attached to and eccentrically disposed on one side of said mouth-piece to allow disengagement or locking by a simple rotation about said pivot-pin axis of said body portion with respect to said mouth-piece;
    D. a latching means for releasably securing said mouth-piece and said body portion when pivoted into register; and
    E. a capsule-piercing means on said body portion for selectively perforating said capsule, whereby said medicaments are released when air is drawn into said air intake passage and swirled about within said chamber.

2. The inhaler of claim 1 wherein a lateral projection is attached to said pin at the end thereof and said hole has an axially disposed enlarged section, which is adapted for slidingly receiving said lateral projection, and an annular enlargement at the end thereof which is adapted to receive and retain said lateral projection when said pivot pin is rotated.

3. The inhaler of claim 1 wherein said latching means comprises an L-shaped projection, which is attached to said mouth-piece and projects outwardly toward said body portion and in the direction of said pivoting, and an L-shaped recess in said body portion which is adapted to receive said L-shaped projection when said mouth-piece and said body portion are in register.

4. The inhaler of claim 3 wherein said latching means further comprises a plunger having a convexly curved end and a compression spring which fit slideably within a longitudinally disposed bore within said body portion and communicating with said L-shaped recess, said plunger being adapted to project into said L-shaped recess and be biasedly depresses by said L-shaped projection.

5. The inhaler of claim 1 wherein said chamber is cylindrical and comprises an elongated recess in an end wall thereof, said elongated recess being only slightly larger than said capsule.

6. The inhaler of claim 5 wherein said capsule-piercing means is attached to said body portion and comprises a sharpened pin which is adapted to pass through an opening into said elongated recess.

7. An inhaler for administering powdered medicaments, comprising:
    A. a mouth-piece, comprising:
        1. an ellipsoidal tuburlar portion, having a major axis in cross section, with a coaxially disposed inhalation passage therein,
        2. an enlarged basal end which is attached to said tubular portion,
        3. a pivot pin, having two ends, which:
            a. is rigidly attached at one of said two ends to said basal end and eccentrically disposed thereon on one side of said tubular portion,
            b. has a pivot-pin axis which is disposed in parallel to the axis of said tubular portion, and
            c. has a rigidly attached lateral projection which is diposed at the other of said two ends,
        4 an L-shaped projection which:
            a. is rigidly attached at one end to said basal end along one side thereof, and
            b. has on the other end thereof a rigidly attached latching lug which projects laterally but obliquely toward said major axis; and
        5. a grating attached to said tubular portion and across said inhalation passage;
    B. a body portion, comprising:
        1. an upper face which engages said basal end when said mouth-piece and said body portion are assembled, 2. a circular recess in said upper face, having tangentially disposed narrow recesses in communication therewith,
3. an elongated recess, disposed in said circular recess, which is adapted for receiving a capsule containing said powdered medicaments,
4. a hole which:
   a. is disposed eccentrically to said axis of said tubular portion,
   b. has an elongated lateral enlargement in the perimeter thereof that accomodates said lateral projection when said mouth-piece and said tubular portion are revolved to and past a loading position which exposes said chamber,
   c. extends from said upper face into said body portion for a distance equalling the distance along said pivot pin from said basal end face to said lateral projection; and
   d. terminates in an enlarged annular section which accommodates said lateral projection as it revolves around said pivot-pin axis while said mouth-piece and said body portion relatively revolve about said pivot-pin axis;
5. an L-shaped recess which:
   a. is disposed along one side of said body portion and is laterally open,
   b. is obliquely disposed to said elongated recess, and
   c. has a laterally projecting latching slot into which said latching lug revolvingly fits when said body portion and said mouth-piece are mutually revolved from said loading position to an operating position in which said circular recess is aligned with said tubular portion; and
C. a selectively operable capsule-piercing means for perforating said capsule, whereby said capsule is stored in sealed condition while said inhaler is in said operating position and said medicaments are released after said capsule is pierced and air is drawn into said narrow recesses and swirled about within said chamber.

8. The inhaler of claim 7 which further comprises a cover having a generally oval cross-section with a major axis coinciding with said major axis of said ellipsoidal tubular portion and a pair of oppositely disposed side flaps which cover said narrow recesses when said cover is placed over said mouth-piece.

9. In an inhaler for administering powdered medicaments from a selectively pierced capsule, said inhaler having a tubular portion with a coaxially disposed inhalation passage therein and a body portion with an elongated recess for depositing said capsule therein, the improvement comprising:
A pivot means for mutually revolving said tubular portion and said body portion from a closed operating position, in which said elongated recess is aligned with said passage and protectively covered by said tubular portion, to an open loading position, in which said elongated recess is exposed for said depositing said capsule; and furhter from said open loading position to a separating position, in which said tubular portion and said body portion are axially movable apart;
B. a retaining means for maintaining said body portion and said tubular portion in revolvable relationship while mutually revolving from said opening position to said separating position;
C. a joining-and-separating means, attached to said pivot means, for permitting said tubular portion and said body portion to be axially moved apart in endwise sliding relationship while said inhaler is in said separating position;
D. a latch means for revolvingly engaging said body portion and said tubular portion in said operating position; and
E. an air inlet means, comprising narrow recesses in said body portion, for admitting air into said inhaler in said operating position and for permitting visual inspection and cleaning of said narrow recesses when said inhaler is in said loading position.

10. The improvement in the inhaler of claim 9 wherein said pivot means comprises a pivot pin which is rigidly attached at its inner end to said tubular portion and a hole which extends from its outer end into said body portion and further comprises eccentrically disposing said pivot pin on said tubular portion and eccentrically disposing said hole in said body portion so that said pivot pin and said hole fit slidingly and rotatingly and are coaxially aligned.

11. The improvement in the inhaler of claim 10 wherein said retaining means comprises a lateral projection, disposed at the outer end of said pivot pin and extending laterally beyond said hole, and a lateral enlargement, disposed at the inner end of said hole, which accommodates revolving movement of said lateral projection while said tubular portion and said body portion are being mutually revolved from said operating position to and through said loading position and to said joining-and-separating position and which prevents said endwise sliding.

12. The improvement in the inhaler of claim 11 wherein said joining-and-separating means comprises, in combination, said lateral projection and an elongated lateral enlargement of said hole which slidingly fits said lateral projection, said lateral projection and said lateral enlargement being in register only when said tubular portion and said body portion are in said separating position and being more than 180° out of register, measured through said loading position, when said tubular portion and said body portion are in said operating position.

13. In an inhaler for powered medicaments contained in a capsule, the improvement comprising a means for charging said inhaler with said capsule while maintaining said inhaler in connected relationship, comprising:
A. an elongated mouth-piece, comprising on one end an air outlet and on the other end a pivotal securing means,an eccentrically mounted pivot pin, a latch, an air-pervious capsule-retaining means, and an air passage connecting said air outlet and said air-pervious capsule-retaining means; and
B. a base, comprising an eccentrically mounted pivot-pin receiving means, a latch keeper, an air inlet, a capsule chamber of a size to loosely hold said capsule, and a radially extending piercing means for said capsule, whereby operation of said inhaler enables said capsule to be charged into said capsule chamber when said mouth-piece and said base are pivotably separated and enables air to be drawn through said air inlet into said capsule chamber and through said air passage to said air outlet when said mouth-piece and said base are pivotably aligned.

14. The improvement in the inhaler of claim 13, wherein said base has an ellipitical shape and wherein said elongated mouth-piece is covered and enclosed by a cap, having said elliptical shape, which contacts both said air outlet and said base when said mouth-piece and said base are pivotably aligned.

15. The improvement in the inhaler of claim 13 wherein said cap has a pair of wing flaps which contact said radially extending piercing means when said mouth-piece and said base are pivotably aligned.

16. The improvement in the inhaler of claim 13 wherein said radially extending piercing means is spring biased.

17. The improvement in the inhaler of claim 13, wherein said capsule chamber comprises an elongated capsule recess, within which said capsule fits loosely and into which said capsule is charged, and a cylindrically shaped spinning chamber which is operably connected to said elongated capsule recess and to said air-pervious capsule-retaining means when said mouth-piece and said base are pivotably aligned.

18. The improvement in the inhaler of claim 17 wherein said air inlet is tangentially disposed in relation to said capsule chamber, whereby said operation of said inhaler produces a rush of air through said air inlet into said capsule chamber to create a vortex therein which lifts said capsule from said capsule recess into said cylindrical spinning chamber and spins it therewithin.

* * * * *

UNITED STATES PATENT OFFICE
CERTIFICATE OF CORRECTION

Patent No. 3,991,761            Dated November 16, 1976

Inventor(s) Salvatore Cocozza           Page 1 of 2

It is certified that error appears in the above-identified patent and that said Letters Patent are hereby corrected as shown below:

Col. 1, line 40, after "intake" insert --passages are positioned in such a way that a capsule--.

Col. 1, line 50, "by" should be --but--.

Col. 1, line 52, "revoloution" should be --revolution--.

Col. 2, line 2, after "capsule" insert --chamber--.

Col. 3, line 14, delete "1" at end of line and insert a period --.--.

Col. 5, line 2, after "respect to the", insert --mouthpiece 22 by ribs--.

Col. 5, line 4, change "opend" to --opened--.

Col. 5, line 5, change "moth" to --mouth--.

Col. 5, line 7, after "into" insert --position into--.

Col. 5, line 52, Claim 1, after "is" insert --in--.

Col. 6, line 44, Claim 7, "tuburlar" should be --tubular--.

UNITED STATES PATENT OFFICE
CERTIFICATE OF CORRECTION

Patent No. 3,991,761　　　　　　　　　　Dated November 16, 1976

Inventor(s) Salvatore Cocozza　　　　　　　Page 2 of 2

It is certified that error appears in the above-identified patent and that said Letters Patent are hereby corrected as shown below:

Col. 6, line 67, Claim 7, "moutht" should be --mouth--.

Col. 7, line 61, Claim 9, change "furhter" to --further--.

Col. 7, line 67, Claim 9, change "opening" to --operating--.

Signed and Sealed this

Tenth Day of May 1977

[SEAL]

Attest:

RUTH C. MASON　　　　　　　　　　C. MARSHALL DANN
*Attesting Officer*　　　　　　　　*Commissioner of Patents and Trademarks*